United States Patent [19]

Farrish

[11] Patent Number: 4,767,786

[45] Date of Patent: Aug. 30, 1988

[54] DISINFECTANT AND CLEANSING COMPOSITION

[75] Inventor: James H. Farrish, Houston, Tex.

[73] Assignee: Fhj Amino Acid Formula Trust, Santa Rosa Beach, Fla.

[21] Appl. No.: 53,575

[22] Filed: May 22, 1987

Related U.S. Application Data

[63] Continuation of Ser. No. 805,024, Dec. 5, 1985, abandoned, which is a continuation of Ser. No. 667,313, Nov. 1, 1984, abandoned, which is a continuation of Ser. No. 563,471, Dec. 20, 1983, abandoned, which is a continuation of Ser. No. 397,380, Jul. 12, 1982, abandoned, which is a continuation of Ser. No. 280,030, Jul. 2, 1981, abandoned, which is a continuation of Ser. No. 160,337, Jun. 17, 1980, abandoned, which is a continuation of Ser. No. 15,554, Feb. 26, 1979, abandoned.

[51] Int. Cl.[4] ................ A61K 31/195; C11D 3/26
[52] U.S. Cl. ................................. 514/561; 252/546
[58] Field of Search ..................... 514/561; 252/546

[56] References Cited

U.S. PATENT DOCUMENTS

| | | | |
|---|---|---|---|
| 3,075,924 | 1/1963 | Rubin | 252/546 |
| 3,151,084 | 9/1964 | Schiltz et al. | 252/137 |
| 3,492,238 | 1/1970 | Wohlberg | 252/148 |
| 3,920,020 | 11/1975 | Kraskin | 604/359 |
| 3,935,862 | 2/1976 | Kraskin | 604/360 |
| 4,107,331 | 8/1978 | Rosenberg | 514/567 |

OTHER PUBLICATIONS

McCutcheon's; Detergents and Emulsifiers, (1967), 39, 54, 79, 96, 150 and 270.
McCutcheon's; Detergents and Emulsifiers, (1973), 9 & 63.

*Primary Examiner*—Allen J. Robinson
*Attorney, Agent, or Firm*—Finnegan, Henderson, Farabow, Garrett and Dunner

[57] ABSTRACT

A disinfectant and cleansing composition is provided which contains as primary active ingredient an alkali metal salt of a hydroxy alkyl amine-substituted carboxylic acid, e.g., sodium dihydroxy ethyl glycine. In a preferred embodiment, the composition contains as primary active ingredients a mixture of a major proportion of said alkali metal salt of hydroxy alkyl amine-substituted carboxylic acid and a minor proportion of an anionic surface active agent, e.g., sodium diisobutyl naphthalene sulfonate, in an inert carrier therefor, e.g., water. Methods are disclosed for using said compositions including disinfecting objects and surfaces thereof, particularly animate objects and surfaces, and animal tissue such as the human skin, and reducing pain and relieving itching of animal tissue such as the human skin.

6 Claims, No Drawings

DISINFECTANT AND CLEANSING COMPOSITION

This application is a continuation of application Ser. No. 805,024, filed Dec. 5, 1985, now abandoned, which was a continuation of application Ser. No. 667,313, filed Nov. 1, 1984, now abandoned, which was a continuation of application Ser. No. 563,471, filed Dec. 20, 1983, now abandoned, which was a continuation of application Ser. No. 397,380, filed July 12, 1982, now abandoned, which was a continuation of application Ser. No. 280,030, filed July 2, 1981, now abandoned, which was a continuation of application Ser. No. 160,337, filed June 17, 1980, now abandoned, which was a continuation of application Ser. No. 15,554, filed Feb. 26, 1979, now abandoned.

The present invention relates to disinfectant and cleansing compositions and methods of use thereof. More particularly, the present invention relates to compositions which are effective for disinfecting (i.e., destroying harmful microorganisms) and cleansing, for example, animate objects and surfaces. In one preferred embodiment, the composition of the present invention is useful in disinfecting and cleansing animal tissue such as the human skin while, at the same time, significantly reducing pain and itching without causing irritation or other harmful effects on the skin.

Alkali metal salts of hydroxy alkyl amine-substituted carboxylic acids are known as chelating agents useful, for example, for the chelating of iron in metal cleaning. However, chelating agents in general have been believed to be ineffective anti-bacterial agents. Moreover, due to the high pH of commercially available solutions of the alkali metal salts of hydroxy alkyl aminesubstituted carboxylic acids, generally in the neighborhood of 13–14, it has been believed that they would be harmful and even destructive to animal tissue, e.g., human skin.

Conventional anionic surface active agents are known as excellent cleansing agents. However, the anionic surface active agents are also known as tending to irritate animal tissue, e.g., the human skin, by interaction with the protein of the tissue. Moreover, the conventional anionic surface active agents have at most only a very slight bactericidal action and have been taught as destroying the bactericidal action of known bactericides such as the cationic surface active agents.

It is a primary object of the present invention to provide a disinfectant and cleansing composition which is effective for destroying harmful microorganisms on, for example, animate objects and surfaces.

It is a further object of the present invention to provide such a composition which is effective in disinfecting and cleansing animal tissue without causing irritation or other harmful effects and also effective in reducing pain and itching.

Still further objects and the entire scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art therefrom.

Surprisingly, it has now been found according to the present invention that a composition containing as primary active ingredient an alkali metal salt of a hydroxy alkyl amine-substituted carboxylic acid is effective in fulfilling the above objects. In another preferred embodiment, it has been found that a combination of a major proportion of the alkali metal salt of hydroxy alkyl amine-substituted carboxylic acid with a minor proportion of an anionic surface active agent produces a disinfectant and cleansing composition which may exhibit a synergistic effect in fulfilling the above objects. The composition of this embodiment is characterized in that it contains as the active components said alkali metal salt compound and said anionic surface active agent.

One particularly suitable alkali metal salt of a hydroxy alkyl amine-substituted carboxylic acid is sodium dihydroxy ethyl glycine available as Hampshire DEG (W. R. Grace & Co.). Other alkali metal salts which may be used include sodium bis N,N-2-hydroxy propyl glycinate, sodium dihydroxy ethyl serinate, sodium bis N,N-2-hydroxy propyl serinate, sodium dihydroxy ethyl alaninate and sodium bis N,N-2-hydroxy propyl alaninate. The potassium salts may also be used. Generally, the alkali metal (preferably sodium or potassium) salts of any hydroxy alkyl (preferably lower alkyl) substituted amine-substituted carboxylic acids may be used. The preferred alkali metal salts are those of the low molecular weight hydroxy alkyl amine-substituted carboxylic acids.

It is important to expose the alkali metal salt to the atmosphere at ambient or slightly elevated temperatures to allow volatilization if any un-realted starting materials, e.g., amines.

A particularly suitable anionic surface active agent is sodium diisobutyl naphthalene sulfonate and others which may be used include sulfated and sulfonated aliphatic and aromatic hydrocarbons; and sulfated and sulfonated esters, amides and alcohols.

Both of the alkali metal salts of hydroxy alkyl amine-substituted carboxylic acids and the anionic surface active agents are known compounds and may be produced in manners known to the art.

The compositions of the present invention may contain broadly from 0.001 to about 47% by weight of the active ingredient, i.e., the alkali metal salt of a hydroxy alkyl amine-substituted carboxylic acid. The Hampshire DEG, for example, is available commercially in solutions containing 46–48% of the salt. For certain purposes, the commercial product may be further concentrated, e.g., by removal of small portions of the solvent by evaporation or other conventional methods, to above about 47% by weight, for example, for up to about 50% by weight or slightly higher of the active ingredient, although this is not ordinarily necessary. The composition may also be diluted by addition of solvent or other inactive carrier. For most external applications, the composition will contain at least about 4–5% by weight of the active ingredient.

For the compositions of the present invention also containing the anionic surfactant, the proportions of active ingredients correspond to from 1 to 9 parts, preferably about 9 parts, by weight of a 40% by weight solution of the anionic surface active agent combined with each part of a 46%–48% by weight solution of the alkali metal salt component. It is to be understood that these proportions may be accomplished in a variety of manners known to the art. Thus, the strengths of the solutions may be varied or the anionic surface active agent may be added in the solid form to the solution of the alkali metal salt component, so long as the final proportions are within the above limitations. Increasing the proportion of anionic surface active agent above about 9 parts by weight may undesirably result in overdrying of animal tissue and perhaps a tendency to irritation.

The solutions of the active components are preferably aqueous solutions, most preferably solutions in deionized water. Other solutions which may be used include those in distilled water or lower alkanols. Mixtures of the solvents may be used.

As discussed hereinbefore, the pH of the alkali metal component in, for example a 46%–48% by weight solution is about 1 13 to 14. Normally, compositions having a pH above about 8 tend to be destructive or otherwise detrimental to animal tissue and this effect normally increases with an increase in the pH. It has been unexpectedly and surprisingly found, however, that the alkali metal salts of hydroxy alkyl amine-substituted carboxylic acids used in the compositions of the present invention are not harmful to animal tissue. While the addition of the anionic surface active agent in the compositions containing same does not significantly reduce the pH of the combination, surprisingly the composition is even less detrimental to animal tissue.

The compositions of the present invention are most effective disinfectants. That is, they will eliminate or at least significantly reduce and control harmful microorganisms including bacteria, fungi, etc. The high pH also is effective in reducing pain, e.g., from burns, perhaps by the production of heat upon contact with the animal tissue. The compositions of the present invention are absorbed rapidly by and into animal tissue such as the human skin. It has been found that the compositions are also effective for application to the teats of milk cows to cleanse and disinfect the teats while preventing irritation thereof.

It is believed that the composition of the present invention which contains the anionic surfactant may exhibit a two-way synergistic safety characteristic. That is, the anionic surface active agent operates synergistically to significantly reduce or eliminate any possible irritating effects resulting from the high pH of the alkali metal salts of hydroxy alkyl amine substituted carboxylic acids, and said alkyl metal salts, in turn, may operate synergistically to significantly reduce or eliminate any harmful effect of the anionic surface active agent such as its known tendency to irritate animal tissue such as the human skin. Most significantly, the two components interact synergistically to provide an effective disinfectant composition useful to eliminating all harmful microorganisms from, for example, animate objects and surfaces.

For purposes of the present invention, the term "animate" is to be understood in its broad sence, i.e., referring to objects and surfaces possessing, or having possessed, life. It is believed, however, that the composition of the present invention may also find use in disinfecting objects and surfaces such as the shells of eggs and as bactericides and/or insecticides.

If desired, the normally high pH of the composition can be reduced by addition of a non-toxic acid, e.g., acetic acid or citric acid. The pH of the composition can be lowered to about 4 with citric acid and to about 3 with acetic acid. It has been surprisingly found that even with lowering of the pH, the composition is still effective although the effect may be retarded somewhat. For example, at a pH of 8, the composition is still an effective disinfectant and still effectively reduces pain and itching.

The compositions of the present invention may be diluted with a carrier, e.g., deionized water, for various purposes. For example, the compositions of the present invention containing from 0.001 to about 5 parts by weight of the active ingredient or ingredients may be ingested orally or given intraperitineal to animals. The compositions may also be concentrated for other purposes, e.g., by volatilization of a portion of the carrier.

Other ingredients may be added to the composition as desired including dyes, pigments, perfumes, etc. up to a total of about 10% by weight. Also, for application to animal tissue such as the human skin, the composition may contain constituents normally present in preparations for this purpose such as emulsifiers, fatty substances, plant extracts, preservatives and solvents in the customary amounts. Thus, the compositions of the present invention may contain any such constituents which are at least miscible with the carrier or solvent, will not be irritating to animal tissue either alone or in combination with the active ingredient or ingredients, and will not materially effect the pH of the composition.

The present invention is illustrated by the following non-limiting examples wherein all parts and percentages are by weight unless otherwise defined.

EXAMPLE 1

A composition was prepared containing 47% by weight of sodium dihydroxy ethyl glycine in water.

EXAMPLE 2

The composition of Example 1 was diluted with 30 parts by weight of water.

EXAMPLE 3

9 Parts of a 46%–48% by weight aqueous solution of sodium dihydroxy ethyl glycine was admixed with stirring with 1 part of a 40% by weight aqueous solution of sodium diisobutyl naphthalene sulfonate.

EXAMPLE 4

The composition prepared according to Example 3 was diluted with 20 parts by weight of deionized water.

EXAMPLE 5

The composition prepared according to Example 3 was concentrated by heating to evaporate the aqueous carrier until the solution contained about 50 parts by weight of active ingredients.

What is claimed is:

1. A method for disinfecting and cleansing, wherein said method comprises:
    topically applying to external animal tissue having bacteria or fungi thereon a composition in an amount sufficient to kill the bacteria or fungi;
    wherein the composition consists essentially of an aqueous solution comprising sodium dihydroxyethyl glycine in a disinfecting amount against bacteria or fungi;
    wherein said sodium dihydroxyethyl glycine has been pretreated at a temperature and for a time sufficient to remove free amines by volatilization to reduce toxicity of the composition to animal tissue.

2. The method as claimed in claim 1, wherein the aqueous solution contains about 4% to 5% by weight of the sodium dihydroxyethyl glycine.

3. The method as claimed in claim 1, wherein the aqueous solution contains from about 0.001 to about 5 parts by weight of the sodium dihydroxyethyl glycine.

4. The method as claimed in claim 1, wherein the aqueous solution contains about 1 to about 9 parts of a 40% by weight solution of sodium diisobutyl naphthalene sulfonate anionic surface active agent for each part of said aqueous solution.

5. The method as claimed in claim 4, wherein the composition contains from 1 to 9 parts by weight of a 40% by weight solution of said anionic surface active agent for each part of a 46%–48% by weight solution of said sodium dihydroxyethyl glycine.

6. The method according to claim 1, wherein the aqueous solution contains about 0.001 to about 50% by weight of the sodium dihydroxyethylglycine.

* * * * *